US009766184B2

(12) United States Patent
Ahner et al.

(10) Patent No.: US 9,766,184 B2
(45) Date of Patent: Sep. 19, 2017

(54) SURFACE FEATURES CHARACTERIZATION

(71) Applicant: Seagate Technology LLC, Cupertino, CA (US)

(72) Inventors: Joachim Walter Ahner, Livermoore, CA (US); Stephen Keith McLaurin, Sunnyvale, CA (US); Samuel Kah Hean Wong, Johor Bahru (MY); Henry Luis Lott, Fremont, CA (US)

(73) Assignee: Seagate Technology LLC, Cupertino, CA (US)

( * ) Notice: Subject to any disclaimer, the term of this patent is extended or adjusted under 35 U.S.C. 154(b) by 0 days.

(21) Appl. No.: 14/927,308

(22) Filed: Oct. 29, 2015

(65) Prior Publication Data

US 2016/0077018 A1    Mar. 17, 2016

Related U.S. Application Data

(63) Continuation of application No. 13/931,266, filed on Jun. 28, 2013, now Pat. No. 9,212,900.

(Continued)

(51) Int. Cl.
  *G01N 21/00* (2006.01)
  *G01N 21/88* (2006.01)
  (Continued)

(52) U.S. Cl.
  CPC ......... *G01N 21/8806* (2013.01); *G01B 11/24* (2013.01); *G01N 21/88* (2013.01);
  (Continued)

(58) Field of Classification Search
  USPC ............... 356/237.1–241.6, 242.1–243.8
  See application file for complete search history.

(56) References Cited

U.S. PATENT DOCUMENTS 4,794,550 A * 12/1988 Greivenkamp, Jr. G01B 11/254
250/550
5,790,252 A * 8/1998 Masumura .............. H01L 22/12
257/E21.53
(Continued)

FOREIGN PATENT DOCUMENTS

CN    1424576 A    6/2003
CN    1434919 A    8/2003
(Continued)

OTHER PUBLICATIONS

PCT International Search Report and Written Opinion dated Dec. 11, 2013 in International Application No. PCT/US13/54584. 13 pages.
(Continued)

*Primary Examiner* — Tri Ton
*Assistant Examiner* — Jarreas C Underwood

(57) ABSTRACT

Provided herein is an apparatus, including two photon emitters and a photon detector array. The two photon emitters are configured to emit photons onto an entire surface of an article. The photon detector array includes a number of photon detectors configured to detect photons scattered from features in the entire surface of the article, wherein the features are less than 500 nm in their largest dimension.

20 Claims, 9 Drawing Sheets

Related U.S. Application Data

Figure 1B:
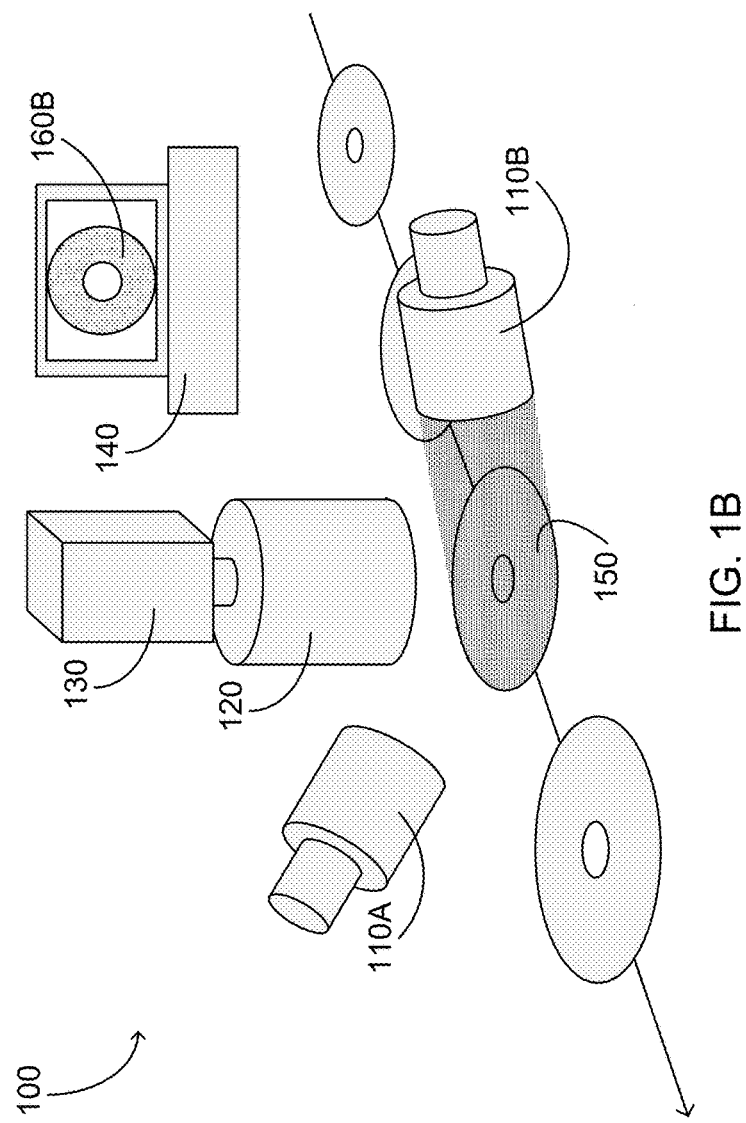

(60) Provisional application No. 61/682,200, filed on Aug. 11, 2012.

(51) Int. Cl.
*G01N 21/17* (2006.01)
*G01N 21/47* (2006.01)
*G01N 21/94* (2006.01)
*G01B 11/24* (2006.01)

(52) U.S. Cl.
CPC .............. *G01N 21/00* (2013.01); *G01N 21/17* (2013.01); *G01N 2201/061* (2013.01)

(56) References Cited

U.S. PATENT DOCUMENTS

| | | | | |
|---|---|---|---|---|
| 6,040,592 A * | 3/2000 | McDaniel | ......... | H01L 27/14609 257/291 |
| 6,392,745 B1 * | 5/2002 | Mavliev | ............ | G01S 17/46 356/3.01 |
| 6,476,908 B1 * | 11/2002 | Watson | ............ | G01J 1/4257 356/214 |
| 6,544,332 B1 * | 4/2003 | Iida | ............ | C30B 29/06 117/19 |
| 6,556,783 B1 * | 4/2003 | Gelphman | ............ | H04N 5/232 348/E5.042 |
| 6,617,087 B1 * | 9/2003 | Rangarajan | ......... | G01N 21/8901 356/237.2 |
| 6,822,734 B1 * | 11/2004 | Eidelman | ............ | G01N 21/8806 356/237.2 |
| 6,879,393 B2 * | 4/2005 | Koizumi | ............ | G01N 21/95607 356/237.4 |
| 7,295,739 B2 * | 11/2007 | Solarz | ............ | G01N 21/8806 359/285 |
| 7,433,031 B2 * | 10/2008 | Xu | ............ | G01N 21/21 356/237.2 |
| 7,474,410 B2 * | 1/2009 | Moon | ............ | B82Y 10/00 356/501 |
| 7,684,057 B2 * | 3/2010 | Sakai | ............ | G01B 11/022 356/614 |
| 7,751,609 B1 * | 7/2010 | Berman | ............ | B24B 37/013 348/125 |
| 8,077,305 B2 * | 12/2011 | Owen | ............ | G01N 21/8806 356/237.1 |
| 8,456,650 B2 * | 6/2013 | Lal | ............ | B82Y 35/00 356/622 |
| 8,547,545 B2 * | 10/2013 | Sasazawa | ............ | G01N 21/8851 356/237.1 |
| 8,665,430 B2 * | 3/2014 | Okamoto | ............ | G01B 9/02 356/124 |
| 2002/0054291 A1 | 5/2002 | Tsai et al. | | |
| 2004/0207836 A1 * | 10/2004 | Chhibber | ............ | G01N 21/4738 356/237.4 |
| 2004/0231177 A1 * | 11/2004 | Mies | ............ | G01B 11/005 33/503 |
| 2004/0246476 A1 * | 12/2004 | Bevis | ............ | G01N 21/474 356/237.5 |
| 2005/0168729 A1 | 8/2005 | Jung et al. | | |
| 2005/0280808 A1 * | 12/2005 | Backhauss | ............ | G01N 21/956 356/237.2 |
| 2007/0206184 A1 | 9/2007 | Uto et al. | | |

FOREIGN PATENT DOCUMENTS

| | | |
|---|---|---|
| CN | 1815206 A | 8/2006 |
| CN | 102141526 A | 8/2011 |
| JP | 2003-028805 A | 1/2003 |
| JP | 2011-185503 A | 9/2011 |
| JP | 2012-042297 A | 3/2012 |

OTHER PUBLICATIONS

PCT International Preliminary Report on Patentability dated Feb. 26, 2015 in International Application No. PCT/US13/54584. 10 pages.
SG Search Report and Written Opinion dated Dec. 17, 2015 in SG Application No. 11201501049Q. 12 pages.
SG Notice of Eligibility for Grant and Examination Report dated Jul. 19, 2016 in SG Application No. 11201501049Q. 5 pages.
CN First Office Action dated Oct. 25, 2016 in CN Application No. 201380053262.8, Includes English Translation. 16 pages.

* cited by examiner

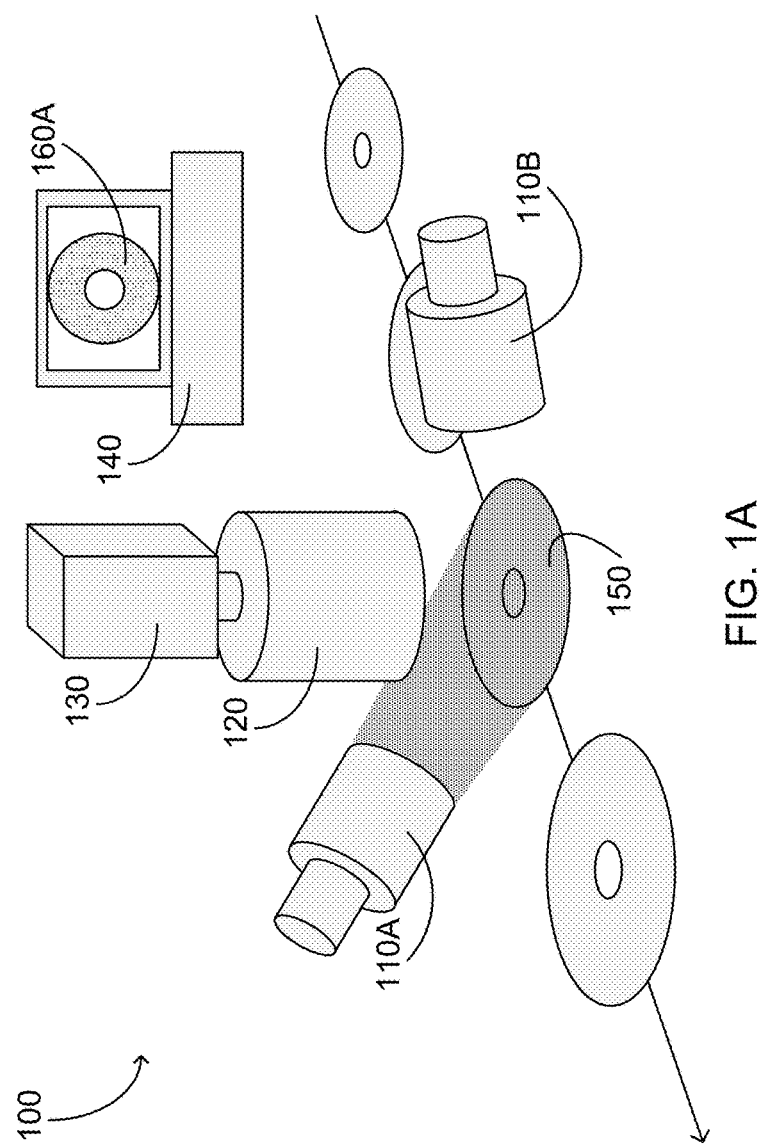

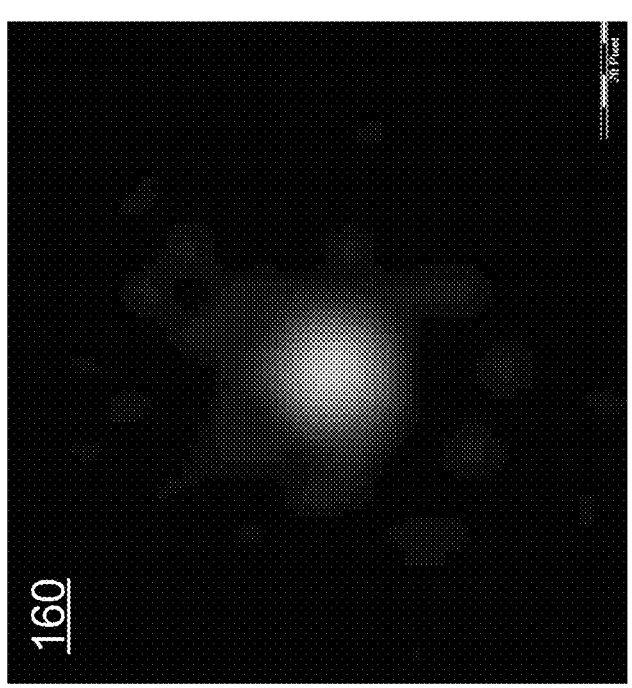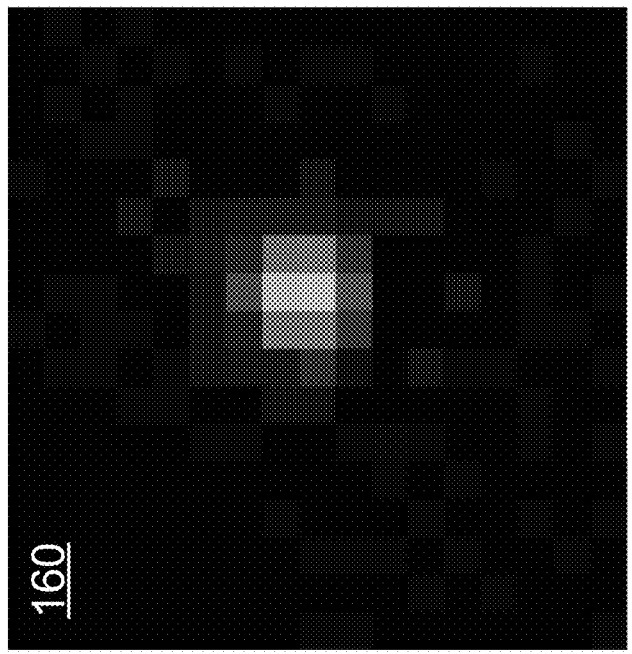
FIG. 6A
FIG. 6B

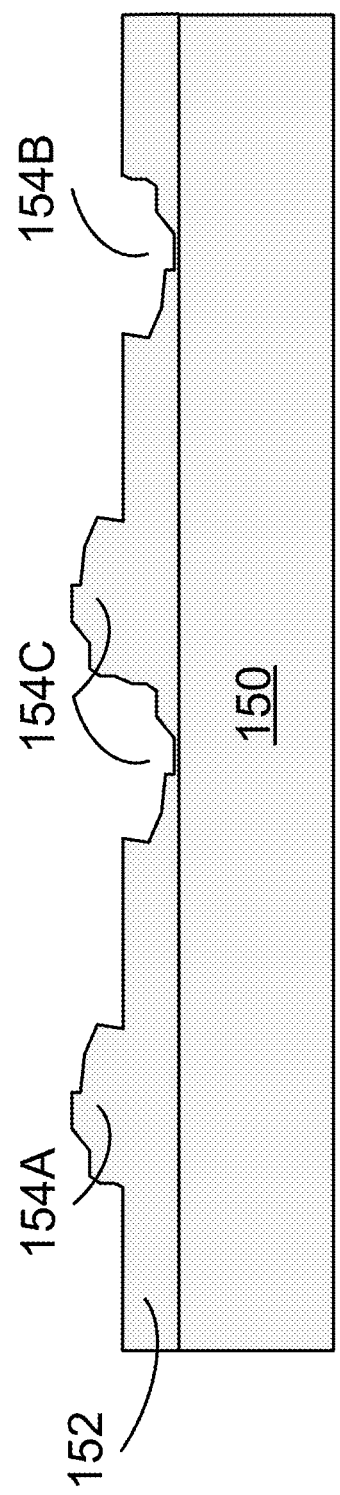

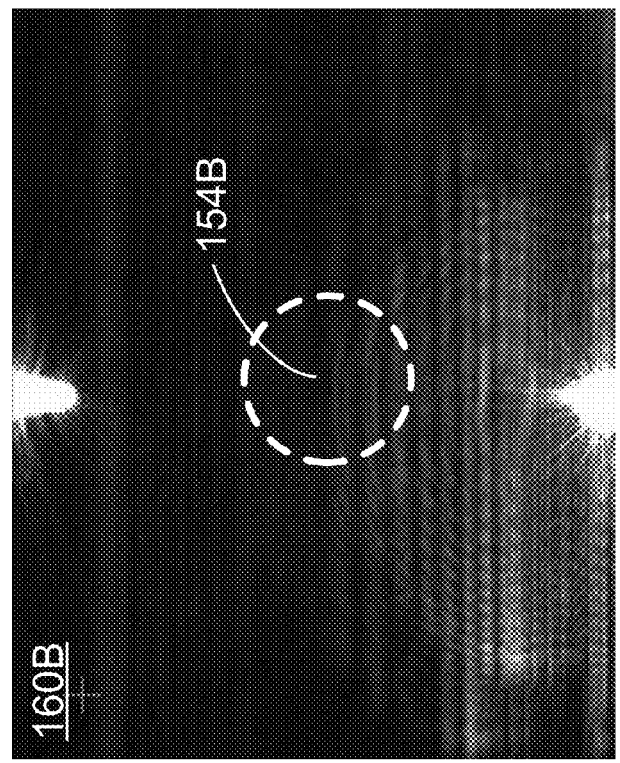
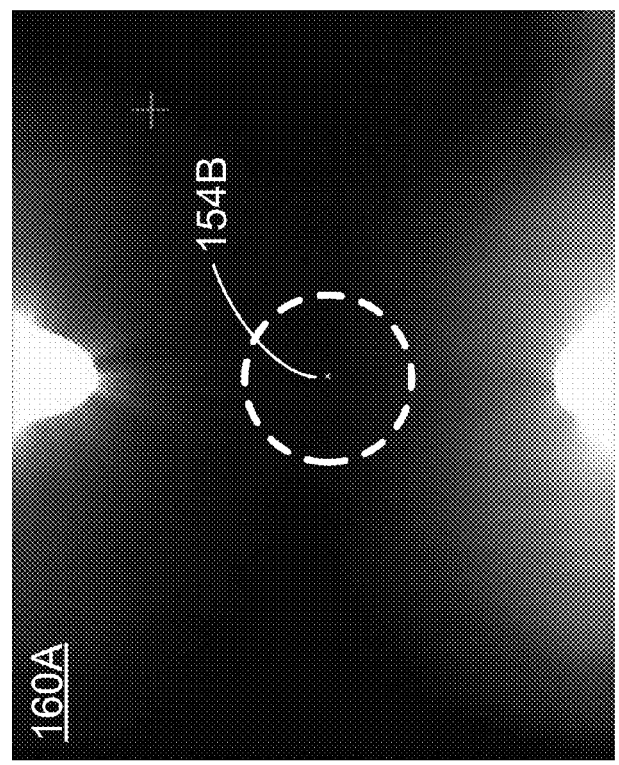

SURFACE FEATURES CHARACTERIZATION

CROSS REFERENCE

This application a continuation of U.S. application Ser. No. 13/931,266 filed Jun. 28, 2013, which claims the priority of U.S. Provisional Patent Application No. 61/682,200, filed Aug. 11, 2012.

BACKGROUND

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Accordingly, apparatuses and methods operable to inspect articles for features such as defects are merited.

SUMMARY

Provided herein is an apparatus, including two photon emitters and a photon detector array. The two photon emitters are configured to emit photons onto an entire surface of an article. The photon detector array includes a number of photon detectors configured to detect photons scattered from features in the entire surface of the article, wherein the features are less than 500 nm in their largest dimension.

These and other features and aspects of the invention may be better understood with reference to the following drawings, description, and appended claims.

DRAWINGS

FIG. 1A provides a schematic illustrating detection of surface features of articles with a photon emitter at a high angle in accordance with an embodiment.

FIG. 1B provides a schematic illustrating detection of surface features of articles with a photon emitter at a low angle in accordance with an embodiment.

Figure 2:
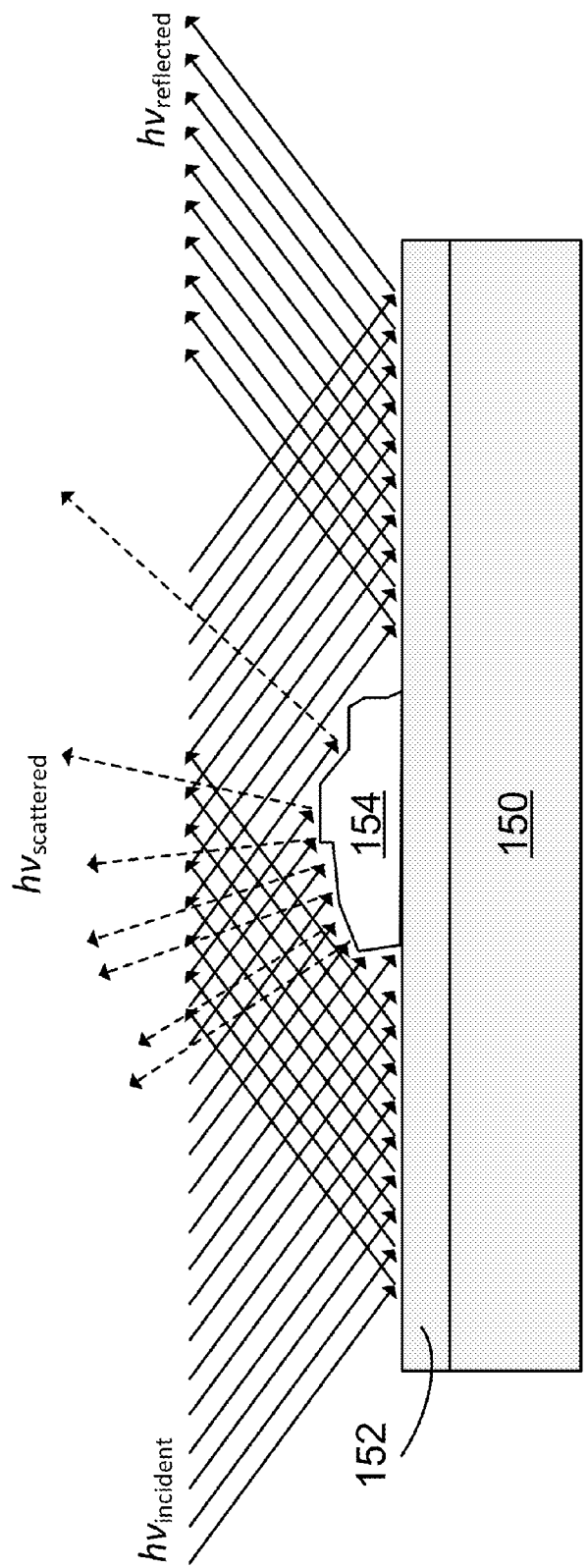

FIG. 2 provides a schematic illustrating photon scattering from a surface feature of an article in accordance with an embodiment.

Figure 3:
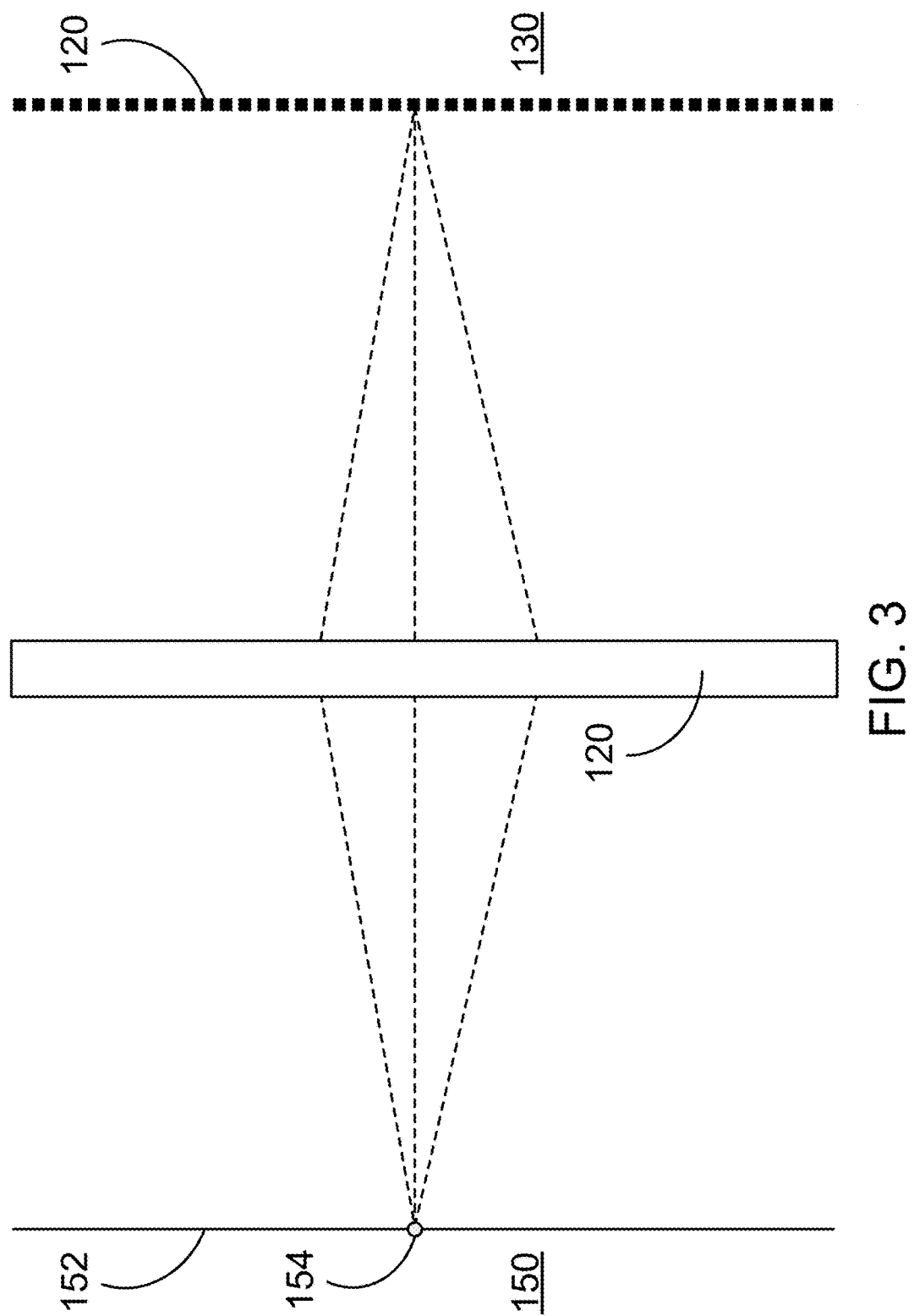

FIG. 3 provides a schematic illustrating photons scattering from a surface feature of an article, through an optical component, and onto a photon detector array in accordance with an embodiment.

Figure 4:
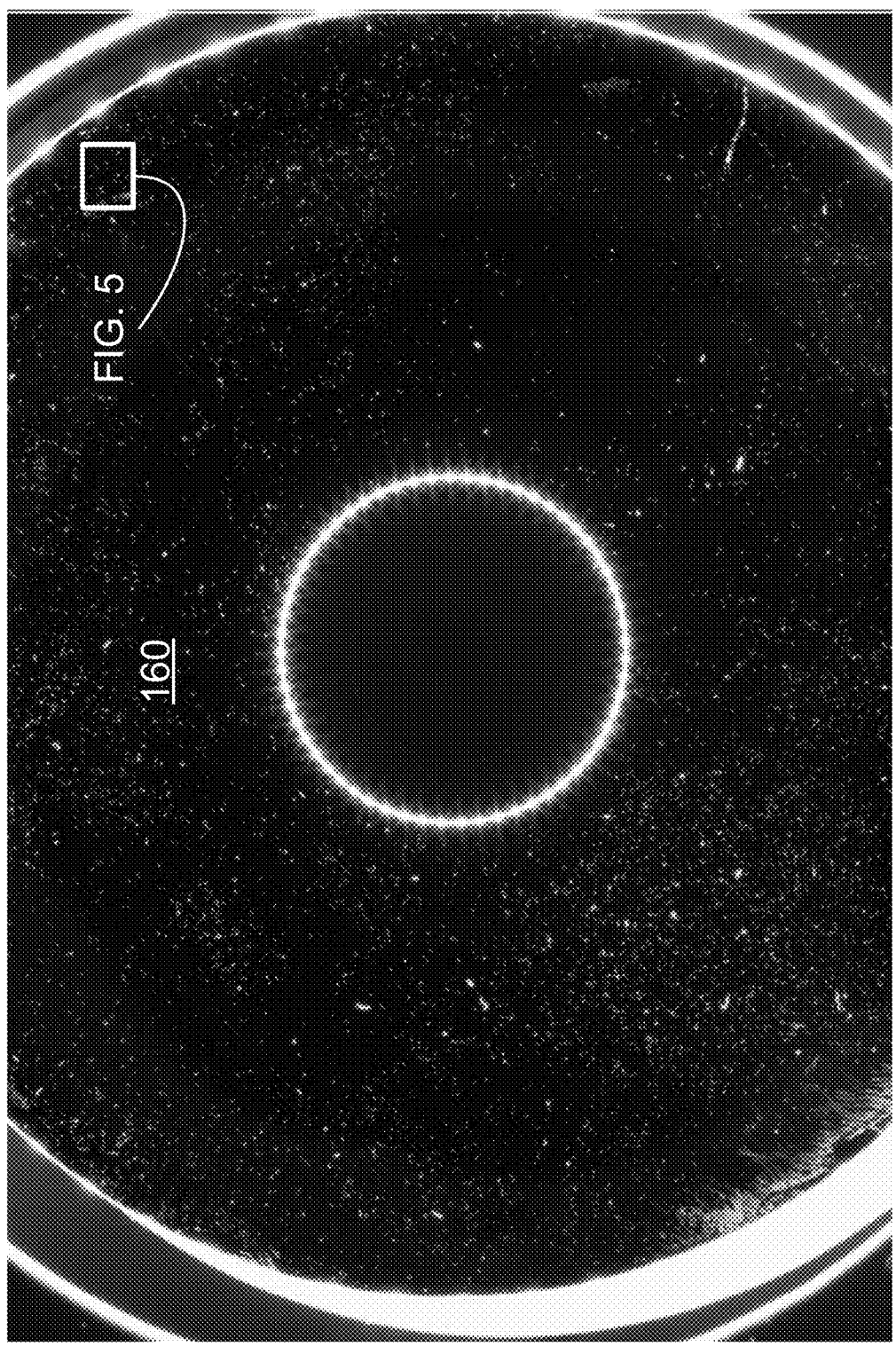

FIG. 4 provides an image of a surface features map of an article in accordance with an embodiment.

Figure 5:
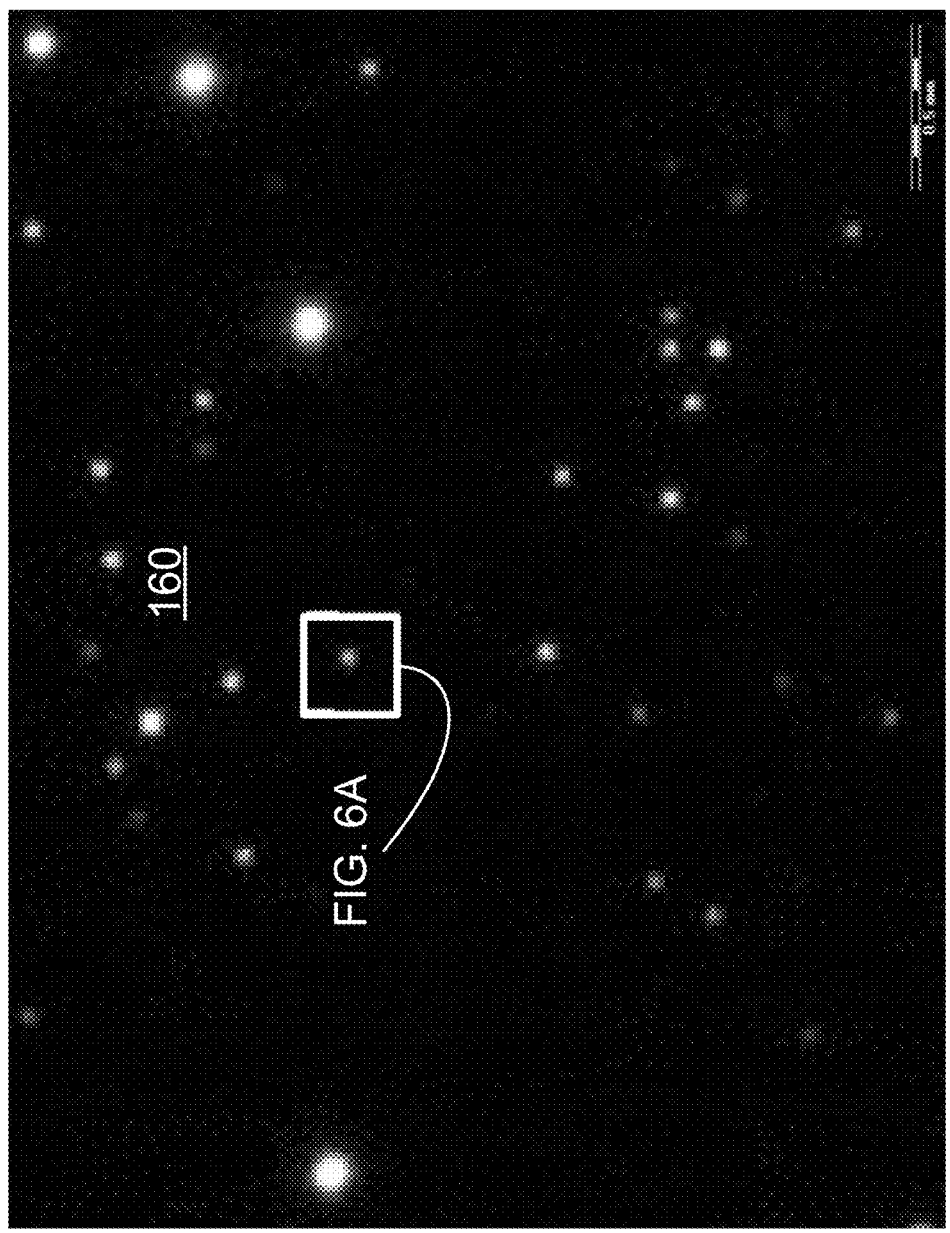

FIG. 5 provides a close-up image of the surface features map provided in FIG. 4.

FIG. 6A (top) provides a close-up image of the surface feature from the map provided in FIG. 5, and FIG. 6A (bottom) provides a photon scattering intensity distribution of the surface feature.

FIG. 6B (top) provides a pixel-interpolated image of the surface feature from FIG. 6A, and FIG. 6B (bottom) provides a pixel-interpolated photon scattering intensity distribution of the surface feature.

FIG. 7 provides a schematic illustrating different surface features of an article in accordance with an embodiment.

FIG. 8A provides a close-up image of a surface features map of an article, wherein a photon emitter is positioned with a relatively high angle with respect to the article's surface, in accordance with an embodiment.

FIG. 8B provides a close-up image of a surface features map of an article, wherein a photon emitter is positioned with a relatively low angle with respect to the article's surface, in accordance with an embodiment.

DESCRIPTION

Before embodiments of the invention are described in greater detail, it should be understood by persons having ordinary skill in the art to which the invention pertains that the invention is not limited to the particular embodiments described and/or illustrated herein, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art to which the invention pertains that the terminology used herein is for the purpose of describing particular embodiments of the invention, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the claimed invention or particular embodiments of the invention. For example, "first," "second," and "third" elements or steps need not necessarily appear in that order, and the claimed invention, or particular embodiments of the invention, need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art to which the invention pertains.

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Provided herein are apparatuses and methods for inspecting articles to detect, map, and/or characterize certain surface features such as surface and/or subsurface defects. Embodiments of the invention will now be described in greater detail.

With respect to articles that may be inspected with apparatuses and methods herein, such articles include any article of manufacture or a workpiece thereof in any stage of manufacture having one or more optically smooth surfaces, examples of which include, but are not limited to, semiconductor wafers, magnetic recording media (e.g., hard disks for hard disk drives), and workpieces thereof in any stage of manufacture. Such articles may be inspected for certain features, including surface and/or subsurface defects that might degrade the performance of the article, which surface and/or subsurface defects include particle and stain contamination, as well as defects including scratches and voids. With respect to particle contamination, for example, particles trapped on a surface of an intermediate hard disk (i.e., workpiece) for a hard disk drive may damage subsequently sputtered films. Particle contamination may also contaminate a finished surface of a hard disk in a hard disk drive, leading to scratch formation and debris generation. Particle contamination of the finished surface of the hard disk may also corrupt the spacing between the hard disk and a read-write head of the hard disk drive, which is also a concern. Differentiating between particle contamination and, for example, voids by characterizing such features minimizes the concern with the spacing between the hard disk and the read-write head while maintaining high product yields. As such, it is important to inspect articles with apparatus and methods herein to correct manufacturing trends leading to surface and/or subsurface defects and to increase product quality.

FIGS. 1A and 1B, in combination, provide schematics for detecting, mapping, and/or characterizing surface features of articles, illustrating an apparatus 100 comprising a pair of photon emitters 110A and 110B, an optical setup 120, a photon detector array 130, and a computer or equivalent device 140, as well as an article 150 and a pair of differential surface features maps 160A and 160B of a surface of the article 150 in accordance with an embodiment. In such an embodiment, photon emitter 110A may be positioned with a relatively high angle for surface features map 160A, and photon emitter 110B may be positioned with a relatively low angle for surface features map 160B. Differential surface features maps 160A and 160B, or the information used to produce surface features maps 160A and 160B, may be used to characterize surface features of articles and differentiate such surface features. The articles and apparatuses of the invention, as well as methods of the invention, are not limited to the embodiment in FIGS. 1A and 1B, as additional embodiments of the invention may be realized by the features described in more detail herein.

An apparatus for detecting, mapping, and/or characterizing surface features of articles may comprise two photon emitters (e.g., see photon emitters 110A and 110B of FIGS. 1A and 1B) or more than two photon emitters, which may be used to emit photons onto a surface of an article, such as the entire surface of the article or some predetermined portion of the surface of the article (e.g., for gradational rotation of the article for piecewise inspection, if desired). In some embodiments, for example, the apparatus may comprise a plurality of photon emitters such as at least 2, 3, 4, 5, 6, 7, 8, 9, or 10 photon emitters. In some embodiments, for example, the apparatus may comprise a plurality of photon emitters such as no more than 10, 9, 8, 7, 6, 5, 4, 3, or 2 photon emitters. Combinations of the foregoing may also be used to describe the foregoing plurality of photon emitters. In some embodiments, for example, the plurality of photon emitters may comprise at least 2 photon emitters and no more than 10 photon emitters (e.g., between 2 and 10 photon emitters), such as at least 2 photon emitters and no more than 6 photon emitters (e.g., between 2 and 6 photon emitters), such as at least 2 photon emitters and no more than 4 photon emitters (e.g., between 2 and 4 photon emitters). Further with respect to the plurality of photon emitters, each photon emitter of the plurality of photon emitters may be the same or different, or some combination thereof (e.g., at least 2 of the same photon emitter, with the remainder of photon emitters being different; at least 4 of the same photon emitter, with the remainder of photon emitters being different; etc.). Even further with respect to the plurality of photon emitters, the photon emitters may be configured in one or more pairs of photon emitters as described herein.

Whether the apparatus comprises two photon emitters or more than two photon emitters, each photon emitter may emit photons onto a surface of an article at a distance and/or an angle optimized for one or more types of features, which types of features are described in more detail herein. Two photon emitters may be paired such that each photon emitter may emit photons onto a surface of an article at a different distance and/or different angle at different times (e.g., sequentially for sequential imaging) for characterization of one or more types of features, which characterization may be accomplished by using two different surface features maps produced under the two photon emitters and/or information used to produce such surface features maps. The angle optimized for one or more types of features may be equal to the glancing angle, which glancing angle is the complement of the angle of incidence, and which angle of incidence is the angle between a ray comprising the emitted photons incident on the surface of the article and the normal (i.e., a line perpendicular to the surface of the article) at the point at which the ray is incident. The glancing angle may also be described as the angle between a ray comprising the emitted photons incident on the surface of the article and the surface at the point at which the ray is incident.

FIG. 2 provides a number of rays comprising emitted photons incident on a surface 152 of an article 150 that form a glancing angle with the surface 152. FIG. 2 further provides a number of rays comprising reflected photons that form an angle of reflection with the normal to the surface, which angle of reflection is equal to the angle of incidence, as well as a number of rays comprising scattered photons from a feature 154 on the surface 152 of the article 150, which rays comprising scattered photons form various scatter angles. A photon emitter may emit photons at a glancing angle ranging from 0° to 90°, wherein a glancing angle of 0° represents the photon emitter emitting photons onto the surface of the article from a side of the article, and wherein a glancing angle of 90° represents the photon emitter emitting photons onto the surface of the article from directly above the article. In some embodiments, for example, a photon emitter may emit photons onto a surface of an article such that the glancing angle is at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon emitter may emit photons onto a surface of an article such that the glancing angle is no more than 90°, 85°, 80°, 75°, 70°, 65°, 60°, 55°, 50°, 45°, 40°, 35°, 30°, 25°, 20°, 15°, 10°, or 5°. Combinations of the foregoing may also be used to describe the glancing angle at which a photon emitter may emit photons onto a surface of an article. In some embodiments, for example, a photon emitter may emit photons onto a surface of an article such that the glancing angle is at least a 0° and no more than 90° (i.e., between 0° and 90°), such as least 0° and no more than 45° (i.e., between 0° and 45°), including at least 45° and no more than 90° (i.e., between 45° and 90°).

The apparatus may comprise a pair of photon emitters (e.g., see photon emitters 110A and 110B of FIGS. 1A and 1B), optionally placed on the same side of the apparatus, wherein each photon emitter may emit photons onto a surface of an article at a different distance and/or different angle at different times (e.g., sequentially for sequential imaging). The pair of photon emitters in such an apparatus may be configured such that a first photon emitter (e.g., photon emitter 110A of FIGS. 1A and 1B) may be positioned with a relatively high angle with respect to an article's surface, and a second photon emitter (e.g., photon emitter 110B of FIGS. 1A and 1B) may be positioned with a relatively low angle with respect to the article's surface. In some embodiments, for example, the first photon emitter may be positioned with a relatively high angle of at least 30°, 35°, 40°, 45°, 50°, 55°, 60°, 65°, 70°, 75°, 80°, or 85°, wherein the angle is the glancing angle. In some embodiments, for example, the first photon emitter may be positioned with a relatively high angle of no more than 90°, 85°, 80°, 75°, 70°, 65°, 60°, 55°, 50°, 45°, 40°, or 35°, wherein the angle is the glancing angle. Combinations of the foregoing may also be used to describe the relatively high angle at which the first photon emitter may be placed with respect to the surface of an article. In some embodiments, for example, the first photon emitter may be positioned with a relatively high angle of at least a 30° and no more than 90° (i.e., between 0° and 90°), such as least 30° and no more than 60° (i.e., between 30° and 60°), including at least 30° and no more than 50° (i.e., between 30° and 50°) and at least 30° and no more than 40° (i.e., between 30° and 40°), wherein the angle is the glancing angle. In some embodiments, for example, the second photon emitter may be positioned with a relatively low angle of at least 0°, 5°, 10°, 15°, 20°, or 25°, wherein the angle is the glancing angle. In some embodiments, for example, the second photon emitter may be positioned with a relatively low angle of no more than 30°, 25°, 20°, 15°, 10°, or 5°, wherein the angle is the glancing angle. Combinations of the foregoing may also be used to describe the relatively low angle at which the second photon emitter may be placed with respect to the surface of an article. In some embodiments, for example, the second photon emitter may be positioned with a relatively low angle of at least 0° and no more than 30° (i.e., between 0° and 30°), such as least 0° and no more than 25° (i.e., between 0° and 25°), including at least 0° and no more than 20° (i.e., between 0° and 20°), at least 0° and no more than 10° (i.e., between 0° and 10°), and at least 3° and no more than 7° (i.e., between 3° and 7°), wherein the angle is the glancing angle. The arrangement of a first photon emitter of a pair of photon emitters at a relatively high angle with respect to an article's surface and a second photon emitter of the pair of photon emitters at a relatively low angle with respect to the article's surface allows for differential scattering of photons from surface features in articles as described herein, which allows for producing differential maps described herein, such as differential surface features maps 160A and 160B of FIGS. 1A and 1B.

A photon emitter may emit photons onto a surface of an article, such as the entire surface or some predetermined portion of the surface (e.g., for gradational rotation of the article for piecewise inspection, if desired). The photon emitter may further emit photons onto the entire surface of the article or some predetermined portion of the surface such that the entire surface or the predetermined portion of the surface is uniformly or homogenously illuminated. Uniformly illuminating the entire surface of the article or some predetermined portion of the surface includes, but is not limited to, subjecting the entire surface of the article or some predetermined portion of the surface of the article to the same or about the same photon energy per unit time (e.g., photon power or photon flux) and/or photon power per unit area (e.g., photon flux density). In radiometric terms, uniformly illuminating includes, but is not limited to, subjecting the entire surface of the article or some predetermined portion of the surface of the article to the same or about the same radiant energy per unit time (e.g., radiant power or radiant flux) and/or radiant power per unit area (e.g., irradiance or radiant flux density).

With the appreciation that photons are the elementary particles of electromagnetic radiation or light, a photon emitter or light source may provide light comprising a relatively wide range of wavelengths (e.g., whole spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., whole spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon emitter or light source may be used in conjunction with one or more optical components of an optical setup to provide light having any of the foregoing qualities.

In view of the foregoing, a photon emitter or light source may comprise a lamp such as a flash lamp, including a high-speed flash lamp, configured to minimize vibration while detecting photons scattered from features in a surface of an article with a photon detector array. In some embodiments, for example, a photon emitter or light source may comprise a high-speed Xe flash lamp such as a 500 W Xe flash lamp to minimize vibration while detecting photons scattered from features in a surface of an article with a photon detector array.

Also in view of the foregoing, a photon emitter or light source may comprise a collimated light source such as a laser, including a combination of lasers, configured to emit photons onto a surface of an article at one or more angles. In some embodiments, for example, a combination of lasers may be provided to a laser beam shaper such that the combination of lasers emits photons onto a surface of an article at one angle. In some embodiments, for example, a combination of lasers may be provided to a laser beam shaper such that the combination of lasers emits photons onto a surface of an article at multiple angles. In some embodiments, for example, at least 2, 4, 6, 8, 10, 12, 14, 16, 18, 20, 22, 24, 26, 28, or 30 lasers, or even more than 30 lasers, may be provided to a laser beam shaper such that the combination of lasers emits photons onto a surface of an article at one or more angles. In some embodiments, for example, no more than 30, 28, 26, 24, 22, 20, 18, 16, 14, 12, 10, 8, 6, 4, or 2 lasers may be provided to a laser beam shaper such that the combination of lasers emits photons onto a surface of an article at one or more angles. Combinations of the foregoing may also be used to describe combinations of lasers provided to a laser beam shaper. In some embodiments, for example, at least 2 lasers and no more than 30 lasers (e.g., between 2 and 30 lasers), such as at least 10 lasers and no more than 30 lasers (e.g., between 10 and 30 lasers), including at least 20 lasers and no more than 30 lasers (e.g., between 20 and 30 lasers), and further including at least 24 lasers and no more than 28 lasers (e.g., between 24 and 28 lasers) may be provided to a laser beam shaper such that the combination of lasers emits photons onto a surface of an article of an article at one or more angles.

Further in view of the foregoing, a photon emitter or light source may comprise a two-dimensional light source such as a combination of point light sources, including a linear combination, an arcuate combination, etc. of point light sources configured to emit photons onto a surface of an article. In some embodiments, for example, a two-dimensional light source may comprise a combination of at least 10, 20, 40, 60, 80, 100, 110, 120, 140, 160, 180, or 200 point light sources, or even more than 200 point sources. In some embodiments, for example, a two-dimensional light source may comprise a combination of no more than 200, 180, 160, 140, 120, 100, 80, 60, 40, 20, or 10 point light sources. Combinations of the foregoing may also be used to describe two-dimensional light sources comprising combinations of point light sources. In some embodiments, for example, a two-dimensional light source may comprise a combination of at least 10 and no more than 200 (e.g., between 10 and 200) point light sources, such as at least 40 and no more than 160 (e.g., between 40 and 160) point light sources, including at least 60 and no more than 140 (e.g., between 60 and 140) point light sources, and further including at least 80 and no more than 120 (e.g., between 80 and 120) point light sources. Such point light sources may be linearly combined to form a two-dimensional light source such as a strip light. Such point light sources may be arcuately combined to form a two-dimensional light source such as a ring light. In some embodiments, for example, a photon emitter or light source may comprise a two-dimensional light source comprising at least 60 point light sources, such as a ring light comprising at least 60 point light sources, including a ring light comprising at least 60 light-emitting diodes ("LEDs"), and further including a ring light comprising at least 100 LEDs. A two-dimensional light source comprising LEDs may comprise white LEDs, wherein each LED has a power of at least 10 mW. An LED-based ring light may enhance features such as scratches (e.g., circumferential scratches) and/or voids in surfaces of articles, especially when the LED-based ring light is configured to emit photons onto the surfaces of the articles with lower angles (e.g., glancing angle equal to or less than 45°).

The apparatus may further comprise an optical setup (e.g., see optical setup 120 of FIGS. 1A and 1B), which optical setup may manipulate photons emitted from one or more photon emitters and/or photons scattered from surface features of articles. With the appreciation that photons are the elementary particles of electromagnetic radiation or light, the optical setup may manipulate light emitted from one or more photon emitters and/or light scattered from surface features of articles. The optical setup up may comprise any of a number of optical components placed in the optical path before an article such that the optical components may be used to manipulate photons/light emitted from one or more photon emitters before uniformly or homogenously illuminating the entire surface or the predetermined portion of the surface of the article. The optical setup up may comprise any of a number of optical components placed in the optical path after an article such that the optical components may be used to manipulate photons/light scattered from features in a surface of the article. The forgoing optical components may include, but are not limited to, optical components such as lenses, mirrors, and filters. With respect to optical components such as filters, such filters may include, for example, wave filters and polarization filters. Wave filters may be used in conjunction with photon emitters described herein to provide light comprising a relatively wide range of wavelengths or frequencies, a relatively narrow range of wavelengths or frequencies, or a particular wavelength or frequency. Polarization filters may be used in conjunction with photon emitters described herein to provide light of a desired polarization including polarized light, partially polarized light, or nonpolarized light.

The optical setup may comprise a single lens or a plurality of lenses, including, but not limited to, a combination of a lens coupled to a photon detector array (e.g., photon detector array 130 of FIGS. 1A and 1B) for collecting and detecting photons scattered from features in a surface of an article. The lens coupled to the photon detector array may be an objective lens, such as a telecentric lens, including an object-space telecentric lens (i.e., entrance pupil at infinity), an image-space telecentric lens (i.e., exit pupil at infinity), or a double telecentric lens (i.e., both pupils at infinity). Coupling a telecentric lens to a photon detector array reduces errors with respect to the position of surface features of articles, reduces distortion of surface features of articles, and/or enables quantitative analysis of photons scattered from surface features of articles, which quantitative analysis includes integration of photon scattering intensity distribution for size determination of surface features of articles.

To detect photons scattered from surface features of articles, an apparatus may further comprise a single photon detector array (e.g., see photon detector array 130 of FIGS. 1A and 1B) comprising a plurality of photon detectors or a plurality of photon detector arrays, each comprising a plurality of photon detectors. In some embodiments, for example, the plurality of photon detector arrays may comprise at least 2, 3, 4, 5, 6, 7, 8, 9, or 10 photon detector arrays. In some embodiments, for example, the plurality of photon detector arrays may comprise no more than 10, 9, 8, 7, 6, 5, 4, 3, or 2 photon detector arrays. Combinations of the foregoing may also be used to describe the plurality of photon detector arrays. In some embodiments, for example, the plurality of photon detector arrays may comprise at least 2 photon detector arrays and no more than 10 photon detector arrays (e.g., between 2 and 10 photon detector arrays), such as at least 2 photon detector arrays and no more than 5 photon detector arrays (e.g., between 2 and 5 photon detector arrays). Further with respect to the plurality of photon detector arrays, each photon detector array of the plurality of photon detector arrays may be the same or different, or some combination thereof (e.g., at least 2 of the same photon detector array, with the remainder of photon detector arrays being different; at least 3 of the same photon detector array, with the remainder of photon detector arrays being different; etc.).

Whether the apparatus comprises a single photon detector array or a plurality of photon detector arrays, each photon detector array may be oriented to detect photons scattered from surface features of an article at a distance and/or an angle for an optimum acceptance of photons (e.g., maximum acceptance of photons with minimum background noise) scattered from one or more types of features, which types of features are described in more detail herein. Likewise, a photon detector array and lens (e.g., telecentric lens) combination may be oriented to collect and detect photons scattered from surface features of an article at a distance and/or an angle for an optimum acceptance of photons scattered from one or more types of features. Such an angle may be the angle between a ray comprising the center line axis of the photon detector array and/or the lens extended to the surface of the article and the normal (i.e., a line perpendicular to the surface of the article) at the point at which the ray is extended. The angle, optionally in combination with an aperture that may be optimally sized for maximum acceptance of photons with minimum background noise, may allow for acceptance of scattered photons having a plurality of scatter angles, which scattered photons may be scattered from one or more types of features. A scatter angle may be different than the angle of reflection, which angle of reflection is equal to the angle of incidence as described herein. FIG. 2 provides a number of rays comprising photons scattered from a feature 154 on a surface 152 of an article 150, which rays represent various scatter angles.

In view of the foregoing, a photon detector array or photon detector array and lens combination may be oriented at an angle ranging from 0° to 90°, inclusive, wherein an angle of 0° represents orientation of the photon detector array or the photon detector array and lens combination at a side of the article, and wherein an angle of 90° represents orientation of the photon detector array or photon detector array and lens combination directly above the article. In some embodiments, for example, a photon detector array or photon detector array and lens combination may be oriented at an angle of at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon detector array or photon detector array and lens combination may be oriented at an angle of no more than 90°, 85°, 80°, 75°, 70°, 65°, 60°, 55°, 50°, 45°, 40°, 35°, 30°, 25°, 20°, 15°, 10°, or 5°, or 0°. Combinations of the foregoing may also be used to describe the angle at which the photon detector array or photon detector array and lens combination may be oriented. In some embodiments, for example, a photon detector array or photon detector array and lens combination may be oriented at an angle of at least a 0° and no more than a 90° (i.e., between 0° and 90°), such as least 0° and no more than 45° (i.e., between 0° and 45°) or at least 45° and no more than 90° (i.e., between 45° and 90°).

The photon detector array, optionally in combination with a lens (e.g., telecentric lens), may detect photons scattered from features in a surface of an article, such as the entire surface of the article or some predetermined portion of the surface of the article. The photon detector array, optionally in combination with a lens (e.g., telecentric lens), may detect photons scattered from features in a surface of an article, such as the entire surface of the article or some predetermined portion of the surface of the article, while oriented at a distance and/or an angle for an optimum acceptance of photons scattered from one or more types of features. As provided herein, the angle for an optimum acceptance of photons scattered from one or more types of features may allow for acceptance of scattered photons having a plurality of scatter angles, which scattered photons may be scattered from one or more types of features.

With the appreciation that photons are the elementary particles of electromagnetic radiation or light, a photon detector array or light detector array may detect light comprising a relatively wide range of wavelengths (e.g., ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon detector array or light detector array may be used in conjunction with one or more optical components of an optical setup to detect light having any of the foregoing qualities.

The photon detector array may comprise a plurality of pixel sensors, which pixel sensors, in turn, may each comprise a photon detector (e.g., a photodiode) coupled to a circuit comprising a transistor configured for amplification. Features of a photon detector array comprising such pixel sensors include, but are not limited to, low temperature operation (e.g., down to −40° C.), low electron noise (e.g., 2-10 $e^-$ RMS; 1 $e^-$ RMS; <1 $e^-$ RMS; etc.), wide dynamic range (e.g., 30,000:1, 8,500:1; 3,000:1; etc.), and/or decreased photon/light collection time. A photon detector array may comprise a large number of pixel sensors (e.g., ≥1,000,000 or ≥1 M pixel sensors) arranged in rows and columns of a two-dimensional array, wherein each pixel sensor comprises a photon detector coupled to an amplifier. In some embodiments, for example, a photon detector array may comprise at least 1 M, 2 M, 3 M, 4 M, 5 M, 6 M, 7 M, 8 M, 9 M, 10 M, or more, pixel sensors arranged in rows and columns of a two-dimensional array. In some embodiments, for example, a photon detector array may comprise no more than 10 M, 9 M, 8 M, 7 M, 6 M, 5 M, 4 M, 3 M, 2 M, or 1 M, pixel sensors arranged in rows and columns of a two-dimensional array. Combinations of the foregoing may also be used to describe the number of pixel sensors in a photon detector array. In some embodiments, for example, a photon detector array may comprise at least 1 M and no more than 10 M (e.g., between 1 M and 10 M) pixel sensors arranged in rows and columns of a two-dimensional array, such as at least 1 M and no more than 8 M (e.g., between 1 M and 8 M) pixel sensors, including at least 1 M and no more than 6 M (e.g., between 1 M and 8 M) pixel sensors, further including at least 2 M and no more than 6 M (e.g., between 1 M and 8 M) pixel sensors, and even further including at least 2 M and no more than 5 M (e.g., between 2 M and 5 M) pixel sensors.

Due to surface reflections of surface features in articles and/or small angle scattering (e.g., 4π scattering), surface features may appear much larger in size enabling pixel sensors larger the than surface features to be used. In some embodiments, for example, a photon detector array may comprise micrometer-sized (i.e., admits of μm units as measured) pixel sensors at least 1 μm, 2 μm, 3 μm, 4 μm, 5 μm, 6 μm, 7 μm, 8 μm, 9 μm, or 10 μm in their smallest dimension. In some embodiments, for example, a photon detector array may comprise micrometer-sized pixel sensors no more than 10 μm, 9 μm, 8 μm, 7 μm, 6 μm, 5 μm, 4 μm, 3 μm, 2 μm, or 1 μm in their smallest dimension. Combinations of the foregoing may also be used to describe dimensions of micrometer-sized pixel sensors in photon detector arrays. In some embodiments, for example, a photon detector array may comprise micrometer-sized pixel sensors at least 1 μm and no more than 10 μm (e.g., between 1 μm and 10 μm) in their smallest dimension, such as at least 1 μm and no more than 7 μm (e.g., between 1 μm and 7 μm), including at least 4 μm and no more than 10 μm (e.g., between 4 μm and 10 μm), and further including at least 4

µm and no more than 7 µm (e.g., between 4 µm and 7 µm). Such micrometer-sized pixel sensors may be used in the apparatus to detect, map, and/or characterize surface features of articles that are more than 100 times smaller than the micrometer-sized pixel sensors.

In view of the foregoing, the single photon detector array or the plurality of photon detector arrays may each comprise a complementary metal-oxide semiconductor ("CMOS") or a scientific complementary metal-oxide semiconductor ("sCMOS"), each of which may optionally be part of CMOS camera or a sCMOS camera, respectively.

FIG. 3 provides a schematic for detection of surface features in an article, illustrating a close-up, cross-sectional view of an apparatus comprising an optical setup and a photon detector array. As shown, article 150 comprises a surface 152 and at least surface feature 154. Photons emitted from a single photon emitter or a plurality of photon emitters may be scattered by the surface feature 154 and collected and detected by a combination comprising an optical setup 120 coupled to a photon detector array 130, which combination may be place at a distance and/or an angle for a an optimum acceptance of photons (e.g., maximum acceptance of photons with minimum background noise) scattered from one or more types of features. The optical setup 120, which may comprise a telecentric lens, may collect and focus the photons scattered from the surface feature 154 onto one or more pixel sensors 132 of photon detector array 130, which one or more pixel sensors each comprises a photon detector coupled to an amplifier. The one or more pixel sensors 132, each of which corresponds to a particular, fixed area on an article's surface and a pixel in a map of the article's surface features, may provide one or more signals to the computer or equivalent device for mapping or otherwise determining the position of the surface feature 154 as shown, for example, in FIG. 6A, which is a close-up image of the map of surface features provided in FIG. 5, which, in turn, is a close-up image of the map of surface features provided in FIG. 4. The computer or equivalent device may subsequently use pixel interpolation for further mapping the surface feature 154 as shown in FIG. 6B.

The apparatus may further comprise one or more computers or equivalent devices (e.g., devices that include primary and/or secondary memory and one or more processing elements operable to carry out arithmetic and logical operations) loaded with instructions making the apparatus operable to, but not limited to, convey each article to the apparatus for inspection; position each article for inspection, optionally including gradational rotation of the article for piecewise inspection; hold or otherwise maintain the position of each article for inspection; insert optical components into the optical setup; remove optical components from the optical setup; position and/or adjust optical components for inspection; move each photon emitter into position for inspection, wherein the position for inspection may include a photon emitter-article distance and/or angle (e.g., glancing angle) optimized for one or more types of features; switch each photon emitter on and off, or otherwise between modes for emitting photons and not emitting photons; move each photon detector array into position for inspection, wherein the position for inspection may include a photon detector array-article distance and/or angle (e.g., scatter angle) optimized for one or more types of features; switch each photon detector array on and off, or otherwise between modes for detecting photons and not detecting photons; process photon detector array signals, optionally including pixel interpolation for better accuracy (e.g., 10× better than pixel size) with respect to the position of surface features; map or otherwise determine the position of surface features of articles from photon detector array signals or processed photon detector array signals (e.g., photon scattering intensity distributions); characterize surface features of articles with respect to type (e.g., particle, stains, scratches, voids, etc.) and/or size (e.g., volume from integration of photon scattering intensity distribution); catalog surface features of articles; and determine trends with respect to surface features of articles.

The apparatus may be operable to detect, map, and/or characterize surface features of articles that are nanometer-sized (i.e., admits of nm units as measured) or smaller in their smallest dimension (e.g., length, width, height, or depth, depending on the surface feature), which features may be smaller than the wavelength of photons/light emitted from a photon emitter of the apparatus. However, the apparatus is not limited to detecting, mapping, and/or characterizing surface features of articles that are nanometer-sized or smaller, as the apparatus may be operable to detect, map, and/or characterize surface features of articles that are micrometer-sized (i.e., admits of µm units as measured) or larger. In some embodiments, for example, the apparatus may be operable to detect, map, and/or characterize surface features of articles smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as surface features of articles smaller than 9 Å, 8 Å, 7 Å, 6 Å, 5 Å, 4 Å, 3 Å, 2 Å, or 1 Å in their smallest dimension. In view of the foregoing, the apparatus may be operable to, in some embodiments, for example, detect, map, and/or characterize surface features of articles between 0.1 nm and 1000 nm, such as between 0.1 nm and 500 nm, including between 0.1 nm and 250 nm, and further including between 0.1 nm and 100 nm, and even further including between 0.1 nm and 80 nm.

The apparatus may be operable to detect, map, and/or characterize certain features, including surface and/or subsurface defects comprising particle contamination in which the particles are nanometer-sized (i.e., admits of nm units as measured) or smaller in their smallest dimension (e.g., length, width, or height). In some embodiments, for example, the apparatus may be operable to detect, map, and/or characterize surface and/or subsurface particles smaller than 125 nm, such as smaller than 100 nm, including smaller than 80 nm, and further including smaller than 10 nm in their smallest dimension. Detecting, mapping, and/or characterizing surface and/or subsurface particles down to the level of 10 nm in height is important for hard disks of hard disk drives, as particles greater than 10 nm in height (e.g., from the surface) may corrupt the spacing between the hard disk and the read-write head of a hard disk drive. In some embodiments, for example, the apparatus may be operable to detect, map, and/or characterize surface and/or subsurface particles as small as or smaller than 4 nm in height.

The apparatus may be operable to detect, map, and/or characterize certain features, including surface and/or subsurface defects comprising scratches (e.g., circumferential scratches) that are micrometer-sized (i.e., admits of µm units as measured) or smaller, such as nanometer-sized (i.e., admits of nm units as measured) or smaller, such as angstrom-sized (i.e., admits of Å units as measured) or smaller, in their smallest dimension (e.g., length, width, or depth). With respect to micrometer-sized scratches, the apparatus may be operable to detect, map, and/or characterize scratches from, for example, 1 µm to 1000 µm in length, which may be significantly longer than the wavelength of photons/light emitted from a photon emitter of the apparatus. In some embodiments, for example, the apparatus may be operable to detect, map, and/or characterize surface features such as defects comprising scratches smaller than 1000 µm, such as smaller than 500 µm, including smaller than 250 µm, further including smaller than 100 µm, and even further including smaller than 50 µm in scratch length. With respect to nanometer-sized scratches, the apparatus may be operable to detect, map, and/or characterize scratches from, for example, 1 nm to 500 nm in scratch width. In some embodiments, for example, the apparatus may be operable to detect, map, and/or characterize surface features such as defects comprising scratches smaller than 500 nm, such as smaller than 250 nm, including smaller than 100 nm, further including smaller than 50 nm, and even further including smaller than 15 nm in scratch width. Surprisingly, due to a high level of spatial coherence, the apparatus may be operable to detect, map, and/or characterize angstrom-sized scratches with respect to scratch depth. In some embodiments, for example, the apparatus may be operable to detect, map, and/or characterize surface features such as defects comprising scratches smaller than 50 Å, such as smaller than 25 Å, including smaller than 10 Å, further including smaller than 5 Å, and even further including smaller than 1 Å (e.g., 0.5 Å) in scratch depth. For example, the apparatus may be operable to detect, map, and/or characterize surface features such as defects comprising scratches smaller than 500 µm in length, smaller than 100 nm in width, and smaller than 50 Å in depth.

The apparatus may be operable to accurately and/or precisely map or otherwise determine the position of a feature on an article's surface (e.g., FIGS. 6A (top) and 6B (top)). With respect to accuracy, the apparatus may be operable to map or otherwise determine the position of a feature on an article's surface within a micrometer-sized (i.e., admits of µm units as measured) radius or better. In some embodiments, for example, the apparatus may be operable to accurately map or otherwise determine the position of a feature on an article's surface within a radius of 100 µm, 90 µm, 80 µm, 70 µm, 60 µm, 50 µm, 40 µm, 30 µm, 20 µm, 10 µm, 9 µm, 8 µm, 7 µm, 6 µm, 5 µm, 4 µm, 3 µm, 2 µm, or 1 µm, or better. Combinations of the foregoing may also be used to describe the accuracy with which the apparatus may map or otherwise determine the position of a feature on an article's surface. In some embodiments, for example, the apparatus may be operable to accurately map or otherwise determine the position of a feature on an article's surface within a radius ranging from 1 µm to 100 µm, such as from 1 µm to 50 µm, including from 1 µm to 30 µm, and further including from 5 µm to 10 µm.

In addition to accurately and/or precisely mapping or otherwise determining the position of a feature on a surface of an article, the apparatus may be operable to accurately and/or precisely determine the photon scattering intensity distribution (e.g., FIGS. 6A (bottom) and 6B (bottom)) of the feature on the surface of the article. Such a photon scattering intensity distribution may be used characterize a surface feature of an article both quantitatively and qualitatively. With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, as well as the number of each type of surface feature on the article. Such characterization information may be cataloged across a plurality of articles and be used to correct manufacturing trends should such features include surface and/or subsurface defects that might degrade the performance of the article.

With respect to qualitative characterization of a surface feature of an article, qualitative characterization includes a determination of the type of surface feature (e.g., particle, stain, scratch, void, etc.) on the article, which determination may be effected by, but is not limited to, analysis of photon scattering intensity distributions. As described herein, the apparatus may comprise a pair of photon emitters (e.g., a pair of photon emitters configured to emit broad spectrum, nonpolarized light; polarized, monochromatic light; etc.), wherein a first photon emitter may be positioned with a relatively high angle with respect to an article's surface, and wherein a second photon emitter may be positioned with a relatively low angle with respect to an article's surface. Depending upon the type of surface feature, a photon scattering intensity distribution for the surface feature produced under the first photon emitter and a photon scattering intensity distribution for the surface feature produced under the second photon emitter may be the about the same or different. With respect to particle-type feature 154A on a surface 152 of an article 150 of FIG. 7, for example, a photon scattering intensity distribution for the particle produced under the first photon emitter (relatively high angle) and a photon scattering intensity distribution for the particle produced under the second photon emitter (relatively low angle) may be the about the same or about unity for a ratio of the photon scattering intensity distribution for the particle produced under the first photon emitter (relatively high angle) and the photon scattering intensity distribution for the particle produced under the second photon emitter (relatively low angle). With respect to void-type feature 154B of FIG. 7, for example, a photon scattering intensity distribution for the void produced under the first photon emitter (relatively high angle) and a photon scattering intensity distribution for the void produced under the second photon emitter (relatively low angle) may be different to the extent that the photon scattering intensity distribution for the void produced under the second photon emitter may be very small or negligible (e.g., see respective close-up image of a void-type feature 154B in FIG. 8B) in comparison to the photon scattering intensity distribution for the void produced under the first photon emitter (e.g., see respective close-up image of the same void-type feature 154B in FIG. 8A). As such, a ratio of the photon scattering intensity distribution for the void produced under the first photon emitter (relatively high angle) and the photon scattering intensity distribution for the void produced under the second photon emitter may be quite large or mathematically undefined. In another example, feature 154C of FIG. 7, which feature 154C may be considered a void with a rim or a void in close proximity to a particle, a photon scattering intensity distribution for the feature 154C produced under the first photon emitter (relatively high angle) and a photon scattering intensity distribution for the feature 154C produced under the second photon emitter (relatively low angle) may be somewhat different in that the photon scattering intensity distribution produced for the feature 154C under the first photon emitter may be similar to that produced for a particle and the photon scattering intensity distribution produced for the feature 154C under the second photon emitter may be greater than that of a void but less than that of a particle. As such, a ratio of the photon scattering intensity distribution for the feature 154C produced under the first photon emitter (relatively high angle) and the photon scattering intensity distribution for feature 154C produced under the second photon emitter may be greater than unity or otherwise between the ratios for the foregoing particle and void. The foregoing photon scattering intensity distributions produced under relatively high-angled and relatively low-angled photon emitters may provide the information, part of the information, or otherwise be incorporated for producing differential maps described herein, such as differential surface features maps 160A and 160B of FIGS. 1A and 1B. As such, in some embodiments, qualitative characterization of one or more surface features of an article may comprise contrasting information used to produce a first map produced under a first photon emitter (relatively high angle) with information used to produce a second map produced under a second photon emitter (relatively low angle) or contrasting the first map produced under the first photon emitter with the second map produced under the second photon emitter or contrasting. Along with quantitative characterization information, such qualitative characterization information may be cataloged across a plurality of articles and be used to correct manufacturing trends should such features include surface and/or subsurface defects that might degrade the performance of the article.

Depending upon factors that may include the type of article, the type of surface features, and the like, it may be desirable at times to increase the number of photons (e.g., photon energy) emitted from a single photon emitter or a plurality of photon emitters to provide an increased scattering signal for characterization (e.g., qualitative and/or quantitative) of surface features of articles. Such an increase in photon energy may be with respect to unit time for increased photon power or photon flux, or with respect to unit area for increased photon flux density. Alternately, or in addition, it may be desirable to increase detection time of a single photon detector array or a plurality of photon detector arrays to detect more photons for accurately and/or precisely mapping or otherwise determining the position of surface features. Alternately to one or both of increasing the photon energy or detection time, or in addition to increasing the photon energy and detection time, it may be desirable at times to minimize background noise including stray light from one or more photon emitters, background light, and/or background fluorescent radiation.

The apparatus described herein may be configured to process or inspect articles at a rate greater than or commensurate with the rate at which the articles or workpieces thereof are produced. In some embodiments, for example, the apparatus may be configured to process or inspect articles at a rate of at least 1, 2, 3, 4, 5, 6, 7, 8, 9, 10, 12, 14, 16, 18, or 20 article(s) per second, which rate may be commensurate with the rate at which the articles or workpieces thereof are produced. In some embodiments, for example, the apparatus may be configured to process or inspect articles at a rate of no more than 20, 18, 16, 14, 12, 10, 9, 8, 7, 6, 5, 4, 3, 2, or 1 article(s) per second, which rate may be commensurate with the rate at which the articles or workpieces thereof are produced. Combinations of the foregoing may also be used to describe the rate at which the articles or workpieces thereof are processed or inspected by the apparatus. In some embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, an article such as a hard disk of a hard disk drive need not be rotated during processing or inspecting. As such, the apparatus may be configured to hold an article stationary while emitting photons onto the surface of the article.

While the apparatus may be configured to process or inspect articles a rate greater than or commensurate with the rate at which the articles or workpieces thereof are produced, the apparatus may operate at a slower rate if needed. In some embodiments, for example, the apparatus may be configured to process or inspect articles at a rate less than one article per second. In such embodiments, for example, the apparatus may be configured to process or inspect articles at a rate less than one article per 5, 10, 25, 50, 75, or 100, or more, second(s).

The apparatus described herein comprising a pair of photon emitters, an optical setup, a photon detector array, and a computer or equivalent device may be fully automated and function in different modes, including, but not limited to, an ultrafast mode, an ultrasensitive mode, and ultrasensitive plus mode. With respect to the ultrafast mode, the apparatus may operate at least 200 times faster than other optical surface analyzers (e.g., KLA-Tencor Candela CS10 or CS20), detect surface features such as defects comprising embedded particles down to at least 100 nm, partially detect surface features such as defects comprising scratches (e.g., nanometer-sized scratches), and provide measurements of roughness. With respect to the ultrasensitive mode, the apparatus may operate at least 50 times faster than other optical surface analyzers, detect surface features such as defects comprising embedded particles down to at least 30 nm, and provide measurements of roughness. With respect to the ultrasensitive plus mode, the apparatus may operate at least 20 times faster than other optical surface analyzers, detect surface features such as defects comprising embedded particles down to at least 30 nm, fully detect surface features such as defects comprising scratches (e.g., nano-scratches), and provide measurements of roughness.

As such, provided herein is an apparatus, comprising two photon emitters configured to emit photons onto a surface of an article; a photon detector array comprising a plurality of photon detectors configured to receive photons scattered from features in the surface of the article; and a mapping means for mapping the features in the surface of the article, wherein the mapping means provides two maps of the features in the surface of the article respectively corresponding to the two photon emitters. In some embodiments, the two photon emitters are positioned on the same side of the apparatus. In some embodiments, the two photon emitters are positioned to emit photons onto the surface of the article at different angles. In some embodiments, a first photon emitter of the two photon emitters is positioned to emit photons onto the surface of the article at a glancing angle of at least 30°, and a second photon emitter of the two photon emitters is positioned to emit photons onto the surface of the article at a glancing angle of less than 30°. In some embodiments, the mapping means comprises one or more computers or equivalent devices loaded with instructions operable to map features in the surface of the article from signals received from the photon detector array. In some embodiments, the apparatus is configured to characterize the features in the surface of the article by contrasting a first map of the two maps with a second map of the two maps. In some embodiments, a first photon emitter of the two photon emitters is configured to emit a first set of photons, a second photon emitter of the two photon emitters is configured to emit a second set of photons, and the apparatus is configured to characterize the features in the surface of the article by contrasting signals from the photon detector array corresponding to the first set of photons scattered from features in the surface of the article with signals from the photon detector array corresponding to the second set of photons scattered from features in the surface of the article. In some embodiments, the apparatus further comprises a telecentric lens coupled to the photon detector array and one or more additional photon emitters, wherein the mapping means provides one or more additional maps of the features in the surface of the article respectively corresponding to the one or more additional photon emitters.

Also provided herein is an apparatus, comprising a plurality of photon emitters configured to emit photons onto a surface of an article at different angles; an objective lens; a photon detector array coupled to the objective lens comprising a plurality of photon detectors configured to receive photons scattered from features in the surface of the article; and a mapping means for mapping the features in the surface of the article, wherein the mapping means provides a plurality of maps of the features in the surface of the article respectively corresponding to the plurality of photon emitters. In some embodiments, the plurality of photon emitters is positioned on the same side of the apparatus. In some embodiments, a first photon emitter of the plurality of photon emitters is positioned to emit photons onto the surface of the article at a glancing angle of at least 30°, and a second photon emitter of the plurality of photon emitters is positioned to emit photons onto the surface of the article at a glancing angle of less than 30°. In some embodiments, the mapping means comprises one or more computers or equivalent devices loaded with instructions operable to map features in the surface of the article from signals received from the photon detector array. In some embodiments, the apparatus is configured to characterize the features in the surface of the article by contrasting a first map of the plurality of maps with a second map of the plurality of maps.

Also provided herein is an apparatus, comprising a photon detector array configured to receive photons scattered from features in a surface of an article; and a characterization means for characterizing the features in the surface of the article, wherein the characterization means contrasts signals from the photon detector array corresponding to two sets of photons scattered from features in the surface of the article, and the two sets of photons respectively originate from photon emitters at different locations. In some embodiments, the apparatus further comprises a telecentric lens, wherein the telecentric lens is coupled to the photon detector array. In some embodiments, a first photon emitter of the photon emitters is configured to emit a first set of photons of the two sets of photons, and a second photon emitter of the photon emitters is configured to emit a second set of photons of the two sets of photons. In some embodiments, the first photon emitter is positioned to emit photons onto the surface of the article at a glancing angle of at least 30°. In some embodiments, the second photon emitter is positioned to emit photons onto the surface of the article at a glancing angle of less than 30°. In some embodiments, the characterization means comprises one or more computers or equivalent devices loaded with instructions operable to characterize surface features of articles with respect to type and/or size. In some embodiments, the apparatus further comprises a mapping means for mapping the features in the surface of the article, and the mapping means provides maps of the features in the surface of the article respectively corresponding to the photon emitters.

Also provided herein is an apparatus, comprising at least two photon emitters configured to emit photons onto a surface of an article; a photon detector array comprising a plurality of photon detectors configured to receive photons scattered from features in the surface of the article; and a mapping means for mapping the features in the surface of the article, wherein the mapping means provides at least two maps of the features in the surface of the article respectively corresponding to the at least two photon emitters. In some embodiments, the apparatus further comprises a telecentric lens, wherein the telecentric lens is coupled to the photon detector array. In some embodiments, each of the at least two photon emitters is positioned to emit photons onto the surface of the article at different angles. In some embodiments, a first photon emitter of the at least two photon emitters is positioned to emit photons onto the surface of the article at a glancing angle of at least 30°. In some embodiments, a second photon emitter of the at least two photon emitters is positioned to emit photons onto the surface of the article at a glancing angle of less than 30°. In some embodiments, the at least two photon emitters are positioned on the same side of the apparatus. In some embodiments, the mapping means comprises one or more computers or equivalent devices loaded with instructions operable to map features in the surface of the article from signals received from the photon detector array. In some embodiments, the apparatus is configured to characterize the features in the surface of the article by contrasting a first map of the at least two maps with a second map of the at least two maps. In some embodiments, a first photon emitter of the at least two photon emitters is configured to emit a first set of photons, a second photon emitter of the at least two photon emitters is configured to emit a second set of photons, and the apparatus is configured to characterize the features in the surface of the article by contrasting signals from the photon detector array corresponding to the first set of photons scattered from features in the surface of the article with signals from the photon detector array corresponding to the second set of photons scattered from features in the surface of the article.

Also provided herein is an apparatus, comprising at least two photon emitters configured to emit photons onto a surface of an article at different angles; an objective lens; a photon detector array coupled to the objective lens comprising a plurality of photon detectors configured to receive photons scattered from features in the surface of the article; and a mapping means for mapping the features in the surface of the article, wherein the mapping means provides at least two maps of the features in the surface of the article respectively corresponding to the at least two photon emitters. In some embodiments, a first photon emitter of the at least two photon emitters is positioned to emit photons onto the surface of the article at a glancing angle of at least 30°. In some embodiments, a second photon emitter of the at least two photon emitters is positioned to emit photons onto the surface of the article at a glancing angle of less than 30°. In some embodiments, the at least two photon emitters are positioned on the same side of the apparatus. In some embodiments, the mapping means comprises one or more computers or equivalent devices loaded with instructions operable to map features in the surface of the article from signals received from the photon detector array. In some embodiments, the apparatus is configured to characterize the features in the surface of the article by contrasting a first map of the at least two maps with a second map of the at least two maps.

Also provided herein is an apparatus, comprising at least two photon emitters configured to emit photons onto a surface of an article; a photon detector array comprising a plurality of photon detectors configured to receive photons scattered from features in the surface of the article; and a characterization means for characterizing the features in the surface of the article, wherein the characterization means contrasts signals from the photon detector array corresponding to at least two sets of photons scattered from features in the surface of the article. In some embodiments, the apparatus further comprises a telecentric lens, wherein the telecentric lens is coupled to the photon detector array. In some embodiments, a first photon emitter of the at least two photon emitters is configured to emit a first set of photons of the at least two sets of photons. In some embodiments, a second photon emitter of the at least two photon emitters is configured to emit a second set of photons of the at least two sets of photons. In some embodiments, the first photon emitter is positioned to emit photons onto the surface of the article at a glancing angle of at least 30°. In some embodiments, the second photon emitter is positioned to emit photons onto the surface of the article at a glancing angle of less than 30°. In some embodiments, the characterization means comprises one or more computers or equivalent devices loaded with instructions operable to characterize surface features of articles with respect to type and/or size. In some embodiments, the apparatus further comprises a mapping means for mapping the features in the surface of the article, wherein the mapping means provides at least two maps of the features in the surface of the article respectively corresponding to the at least two photon emitters. In some embodiments, the mapping means comprises one or more computers or equivalent devices loaded with instructions operable to map features in the surface of the article from signals received from the photon detector array.

While the invention has been described and/or illustrated by means of particular embodiments and/or examples, and while these embodiments and/or examples have been described in considerable detail, it is not the intention of the applicant(s) to restrict or in any way limit the scope of the invention to such detail. Additional adaptations and/or modifications of the invention may readily appear to persons having ordinary skill in the art to which the invention pertains, and, in its broader aspects, the invention may encompass these adaptations and/or modifications. Accordingly, departures may be made from the foregoing embodiments and/or examples without departing from the scope of the invention, which scope is limited only by the following claims when appropriately construed.

What is claimed is:

1. An apparatus, comprising:
   two photon emitters configured to emit photons onto an entire surface of an article, wherein the two photon emitters subject the entire surface of the article to the same photon energy per unit time; and
   a photon detector array comprising a plurality of photon detectors configured to detect photons scattered from features in the entire surface of the article, wherein the features are less than 500 nm in their largest dimension, and wherein further the two photon emitters are configured to minimize vibration while the plurality of photon detectors is detecting the photons scattered from the features.

2. The apparatus of claim 1, wherein the two photon emitters are positioned on the same side of the apparatus.

3. The apparatus of claim 1, wherein the two photon emitters are positioned to emit photons onto the surface of the article at different angles.

4. The apparatus of claim 1, wherein the photon detector array further comprises a telecentric lens larger than the article.

5. The apparatus of claim 1, further comprising a mapping means for mapping the features, wherein the mapping means provides two maps of the features corresponding to the two photon emitters.

6. The apparatus of claim 5, further comprising a characterizing means configured to contrast a first map of the two maps with a second map of the two maps.

7. The apparatus of claim 1, wherein a first photon emitter of the two photon emitters is configured to emit a first set of photons, a second photon emitter of the two photon emitters is configured to emit a second set of photons, and a characterizing means is configured to contrast signals from the photon detector array corresponding to a first set of scattered photons with a second set of scattered photons.

8. The apparatus of claim 1, wherein the photon detector array comprises at least one million pixel sensors.

9. An apparatus, comprising:
   a plurality of point light sources configured to uniformly illuminate a surface of an article at different angles and scatter photons from features on the surface of the article; and
   a photon detector array comprising a plurality of photon detectors configured to detect the features within an accuracy less than 100 um from the scattered photons, wherein the photon detector array is configured to provide information for a first surface feature map and a second surface feature map, and wherein further the plurality of point light sources is configured to minimize vibration while the plurality of photon detectors is detecting the features.

10. The apparatus of claim 9, wherein the photon detector array is further configured to provide information for qualitative characterization of the features.

11. The apparatus of claim 10, wherein the qualitative characterization includes the types of features.

12. The apparatus of claim 9, further comprising a telecentric lens coupled to the photon detector array.

13. The apparatus of claim 9, wherein the photon detector array comprises at least one million pixel sensors.

14. The apparatus of claim 9, wherein the plurality of point light sources comprises five or more point light sources.

15. An apparatus, comprising:
   a first light source configured to provide light at a first angle onto a surface of an article and scatter the first light from particles or defects;
   a second light source configured to provide light at a second angle onto the surface of the article and scatter the second light from the particles or defects; and
   a detector configured to detect the scattered first light and scattered second light, wherein the first light source is configured to minimize vibration while the detector is detecting the scattered first light and the scattered second light.

16. The apparatus of claim 15, wherein the detector comprises a pixel sensor no more than 10 μm in the smallest dimension.

17. The apparatus of claim 15, wherein the light source is a two dimensional light source.

18. The apparatus of claim 15, wherein the first light source is a flash lamp.

19. The apparatus of claim 15, wherein the detector is further configured to provide information for characterization of the particles or defects with respect to type and size.

20. The apparatus of claim 15, wherein the detector is further configured to provide information for mapping the particles or defects in a first map corresponding to the first light source and a second map corresponding to the second light source.

* * * * *